United States Patent [19]

Jordan et al.

[11] Patent Number: 5,008,294

[45] Date of Patent: Apr. 16, 1991

[54] METHODS OF TREATING TUMORS WITH COMPOSITIONS OF CATECHOLIC BUTANES

[75] Inventors: Russell T. Jordan, Fort Collins, Colo; Edward S. Neiss, New Canaan, Conn; Larry M. Allen, Golden, Colo.

[73] Assignee: Chemex Pharmaceuticals, Inc., Denver, Colo.

[21] Appl. No.: 57,481

[22] Filed: Jun. 3, 1987

Related U.S. Application Data

[63] Continuation-in-part of Ser. No. 52,120, May 4, 1987, abandoned, which is a continuation of Ser. No. 699,923, Feb. 11, 1985, abandoned, which is a continuation-in-part of Ser. No. 578,501, Apr. 9, 1984, abandoned, which is a continuation-in-part of Ser. No 465,631, Feb. 10, 1983, abandoned, which is a continuation-in-part of Ser. No. 365,781, Apr. 5, 1982, abandoned, which is a continuation-in-part of Ser. No. 49,886, Jun. 19, 1979, abandoned.

[51] Int. Cl.⁵ ............................................. A61K 31/05
[52] U.S. Cl. ..................................................... 514/731
[58] Field of Search ................................ 514/727, 731

[56] References Cited

U.S. PATENT DOCUMENTS 3,934,034  1/1976  Manning ............................. 514/734
4,695,590  9/1987  Lippman ............................. 514/724

OTHER PUBLICATIONS

"Medicine Based on a Derivative of Pyrocatechol", Special Patent for Medicine, No. 981,050 (France).
"Antipsoriatic Drugs as Inhibitors of Soybean Lipoxygenase, A Possible Mode of Action", Jagadish C. Sircar, et al., *Protagladins Leucotrienes and Medicine*, 1983, vol. II, 373-380.
Smart et al., Rocky Mount. Med. J., Nov. 1970, pp. 39-43.
Bhuvcineswaran et al., Biochem., 11: 85-91, 1972.

*Primary Examiner*—John W. Rollins
*Attorney, Agent, or Firm*—Kenyon & Kenyon

[57] ABSTRACT

The invention relates to methods useful in the treatment of benign, premalignant and malignant solid tumors, especially those of the skin comprising methods for the administration of pharmacologically active compositions containing catecholic butanes. The invention also relates to methods of preventing the occurence of tumors, and the use of catecholic butanes as a sunscreening agent. The preferred catecholic butane is nordihydroguaiaretic acid. The preferred methods of application of the compositions containing catecholic butanes are by topical application and intratumor injection.

34 Claims, No Drawings

METHODS OF TREATING TUMORS WITH COMPOSITIONS OF CATECHOLIC BUTANES

CROSS REFERENCE TO RELATED APPLICATIONS

This application is a continuation-in-part of a copending Application Ser. No. 052,120 filed May 4, 1987, now abandoned, which is a continuation of Application Ser. No. 699,923 filed Feb. 11, 1985, now abandoned, which is a continuation-in-part of Application Ser. No. 578,501 filed Apr. 9, 1984, now abandoned, which is a continuation-in-part of Application Ser. No 465,631, filed Feb. 10, 1983, now abandoned, which is a continuation-in-part of Application Ser. No. 365,781 filed Apr. 5, 1982, now abandoned, which is a continuation-in-part of Application Ser. No. 49,886 filed June 19, 1979, now abandoned.

FIELD OF THE INVENTION

This invention relates to new methods of treating benign, premalignant and malignant solid tumors, particularly those of the skin, comprising the application to said solid tumors of the herein defined catecholic butanes and pharmaceutical formulations containing said catecholic butanes. The methods according to the invention are also effective in preventing the occurrence of benign, premalignant and malignant solid tumors of the skin when applied prophylactically to subjects exposed to a high risk of cancer causing agents, for sensitization of tumors to X-ray radiation and for the treatment of liver cancer. The methods according to the invention are also useful in the treatment of diseases and disorders of the skin such as acne and psoriasis, in aiding the healing of skin wounds and breaks in the skin and for antiviral, antibacterial and antifungal uses.

BACKGROUND

Methods of treating premalignant and malignant growths of the skin have often been traumatic. A common method of treating disorders such as actinic keratosis has been the application of liquid nitrogen to destroy the affected tissue. Epidermal tumors are commonly treated by physical removal through surgery. A method which has been used in the past is chemosurgery through the application of escharotic or fixative chemicals such as zinc chloride. This method has not been found to be particularly effective because of the physical discomfort associated with the use of such materials. It also has the disadvantage of destroying both healthy tissue and the diseased tissue. Neither has the use of known antitumor drugs been found to be particularly effective in the treatment of skin tumors since these drugs are commonly applied systemically resulting in substantial side effects due to their toxicity.

The naturally occurring meso form of the catecholic butane, nordihydroguaiaretic acid [meso-1,4-bis (3,4-dihydroxyphenyl)-2,3-dimethylbutane] ("NDGA") is found in the creosote bush, and its general structure (generic to all of its stereoisomeric forms) is given in Formula (I).

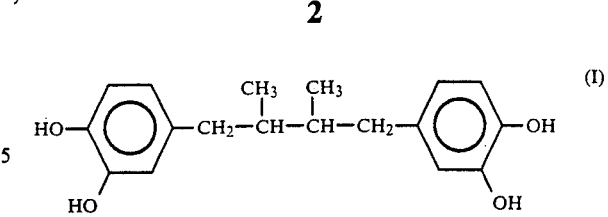

The creosote bush was used for centuries to brew a tea which was the basis for a folk remedy that called for drinking the tea to cure colds, rheumatism and other ailments. However, this remedy has not proven to be successful. NDGA was also used for years as an antioxidant to inhibit the development of rancidity in the fats of food products and as a stabilizer of pharmaceutical preparations, perfumary oils, rubber and other industrial products.

C. R. Smart et al. in the *Rocky Mountain Medical Journal*, Nov. 1970, pp. 39–43, conducted clinical studies to ascertain the validity of an earlier report of tumor regression in a melanoma of a patient taking "Chaparrel Tea", which contains NDGA. In the clinical study conducted by Smart et al., human cancer patients ingested either "Chapparrel Tea", an aqueous extract of Larrea divericata containing NDGA, or doses of pure NDGA. Although some positive results were observed, the authors advised against treatment with "Chaparrel Tea" due to a significant number of reported cases of tumor stimulation. This confirmed the earlier screening studies of NDGA conducted by Leiter et al. of the Cancer Chemotherapy National Service Center of the National Cancer Institute, which obtained negative results when NDGA was tested against several types of cancer cells.

Surprisingly, it has now been discovered that catecholic butanes, particularly nordihydroguaiaretic acid, and/or derivatives thereof as defined herein, in a pharmaceutical composition, are effective in treating benign, premalignant and malignant growths, preferably when directly applied to the situs, without the detrimental side effects associated with chemotherapy or chemosurgical techniques. The compositions provide particularly advantageous results when applied topically to the afflicted area of the skin, or injected into the growth. As disclosed in copending application Ser. Nos. 699,923 and 924,620, such compositions are also effective in treating disorders of the skin including acne and psoriasis, in aiding in the healing of skin wounds and in alleviating bacterial, viral and fungal infections when applied to the situs of the disorder. The compositions are also useful in the treatment of warts.

SUMMARY OF THE INVENTION

This invention relates to methods useful in the treatment and prevention of benign, premalignant and malignant solid tumors, especially those of the skin, comprising the application of pharmaceutical formulations having a catecholic butane of the formula:

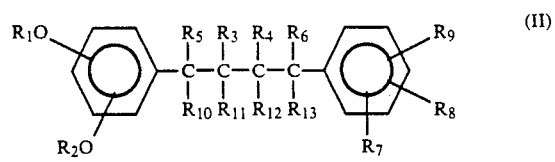

wherein $R_1$ and $R_2$ are independently H, lower alkyl, lower acyl, or alkylene;

$R_3$, $R_4$, $R_5$, $R_6$, $R_{10}$, $R_{11}$, $R_{12}$ and $R_{13}$ are independently H or lower alkyl;

$R_7$, $R_8$ and $R_9$ are independently H, hydroxy, lower alkoxy, lower acyloxy, or any two adjacent groups together may be alkylene dioxy.

Alkylene dioxy generally means methylene (or substituted methylene) dioxy or ethylene (or substituted ethylene) dioxy. Lower alkyl is intended to generally mean $C_1$-$C_6$ alkyl, and preferably $R_3$ and $R_4$ are $C_1$-$C_3$ alkyl. Lower acyl is intended to generally mean $C_1$-$C_6$ acyl, with $C_2$-$C_6$ acyl being preferred. It will be appreciated by those skilled in this art that Formula II is directed to both the phenolic compounds and the conventional esters and ethers thereof.

The invention comprises a method of inhibiting the abnormal growth of cells, such as malignant melanoma cells, human mammary tumor cells, and human lung squamous cell carcinoma cells by contacting the cells with pharmaceutical compositions adapted for topical, parenteral, subcutaneous, or intralesional administration comprising, in admixture with a pharmaceutically acceptable carrier, a catecholic butane of Formula (II). Thus, the invention comprises methods for inhibiting the abnormal growth or proliferation of cells in mammals which preferably comprise applying an amount of said catecholic butane effective to inhibit said abnormal growth directly to the situs of the abnormal growth of cells by topical application or by injection into the interior or near vicinity of the afflicted situs. The preferred compositions comprise nordihydroguaiaretic acid and such compositions in combination with pharmaceutically acceptable carriers.

In a further method of use, the invention comprises a method of preventing the growth of benign, premalignant and malignant cells by prophylactically applying said composition comprising catecholic butanes to a particular body site which may be abnormally exposed to a cancer inducing stimulus.

In a further embodiment, this invention comprises the application of a formulation comprising about 0.05 to about 20 weight percent of substantially pure catecholic butane, NDGA in a preferred embodiment, in combination with a toxicologically acceptable carrier.

DETAILED DESCRIPTION OF THE INVENTION

The term "afflicted situs or area" or similar language, as used herein, refers to a localized area of pathology, infection, wound, lesion, or abnormal cells, including tumors, and the surrounding area.

The term "applying" as used herein embraces both topical applications to a surface of the afflicted situs and injection into the interior of the situs.

The term "mammal" as used herein includes feline, canine, equine, bovine, rodent and primate species, including cats, dogs, horses, rats, mice, monkeys and humans. Other animals e.g., birds, can also be successfully treated with the compositions of this invention.

The term "abnormal growth of cells" refers to benign, premalignant and malignant cells. Examples of the former include the cells associated with adenomas, papillomas, etc. Examples of premalignant cells include actinic keratosis.

The term "escharotic" means a corrosive or caustic agent which is capable of killing healthy, living cells.

The term "solid tumor" refers to tumors in which a plurality of tumor cells are associated with one another, i.e. contiguous and localized within a confined site. This is to be contrasted with "fluid" or "hematogenous" tumors in which the tumor cells occur primarily as unassociated or individual cells, e.g. leukemia. Solid tumors generally propagate on host tissues such as the epithelial, the connective and supportive tissues as well as other tissues located throughout the body. Examples of epithelial tumors include papillomas such as verruca verruciformis and carcinomas such as squamous cell carcinoma, basal cell carcinoma, adenoma, adenocarcinoma, cystadenoma, cystadenocarcinoma and Bowenoid carcinoma. Examples of supportive and connective tissue tumors include sarcomas and their benign counterparts such as fibrosarcoma, fibroma, liposarcoma, lipoma, chondrosarcoma, chondroma, leiomysarcoma, and leimyoma. Examples of other tissue tumors include gliomas (brain tumors) and malignant melanomas.

The term "pharmaceutically-acceptable carrier" refers to a material that is non-toxic, generally inert and does not adversely affect the functionality of the active ingredients.

The methods according to the invention comprising the use of catecholic butanes are surprisingly effective in the treatment of a variety of solid tumors and skin disorders, and are particularly effective when the afflicted areas, or the areas having an abnormal exposure to cancer inducing stimuli, are directly contacted with the instant compositions. The methods according to the invention have unexpectedly been found to provide improved restoration of integrity to injured tissue and cause the regression, elimination or prevention of solid tumors arising from all three embryonic tissue types, namely squamous cell carcinoma, e.g., lung carcinoma, arising from the ectodermal layer; adenocarcinomas, e.g. breast, renal and colon cancer, arising from the endodermal layer; and melanoma and brain cancers, arising from the mesodermal layer.

More specifically, the methods of the instant invention have been found to be effective against the following solid mammalian tumors: mouse Sarcoma-180; human tumors including malignant melanoma, Sarcoma-180, squamous cell carcinoma, lung squamous cell carcinoma, breast adenocarcinoma, glioma, glioastrocytoma, renal-cell carcinoma, colon, Bowenoid carcinoma and basal cell carcinoma; equine tumors including papillomas, malignant melanoma, sarcoid and squamous cell carcinoma; and canine tumors including squamous cell carcinoma, breast adenocarcinoma, perianal adenoma, basal cell carcinoma and mast cell tumor.

The novel methods of this invention are particularly useful in the treatment of keratoses, especially actinic keratosis and senile keratotic lesions, as well as certain cutaneous tumor manifestations of otherwise systemic diseases. The novel methods of the invention have also been found to be effective against equine diseases such as sarcoid, papilloma, malignant melanoma and squamous cell carcinoma, and against canine diseases such as perianal adenoma, mast cell carcinoma, breast adenocarcinoma and malignant melanoma.

The preferred catecholic butane according to the invention, NDGA, has been found to be particularly effective against the following solid human tumors: melanoma (B-16), lung squamous cell carcinoma (LX-1), and human breast adenocarcinoma (MX-1).

It has also been discovered that the catecholic butanes, particularly NDGA, when applied topically, enhance the X-ray radiation effectiveness of the tumor cells without radiation toxicity to surrounding uninvolved skin. Consequently, the catecholic butanes may be useful in the treatment of cutaneous afflictions such as Kaposi's sarcoma.

The invention has also been found to be effective not only in eliminating or ameliorating tumors, but in preventing their occurrence when applied prophylactically. It has been observed that the catecholic butanes are effective in reducing the potential and preventing tumor promotion and in reducing the potential of tumor induction. Thus, the catecholic butanes, e.g., NDGA, are not only effective in preventing cancer formation after cancer induction, but also can be used to prevent cancer development in industrial workers exposed to a carcinogenic agent. In this regard, it is contemplated that the catecholic butanes may be applied prophylactically to a site having abnormal risk to carcinogenic agents or stimuli.

To prevent the establishment of cancer, the catecholic butanes can be formulated into creams and ointments or in cosmetic bases to be used daily, preferably topically. The catecholic butanes can also be used together with a sunscreen to prevent sunlight induction of cancer and sunlight promotion of existing cancers. Surprisingly, the catecholic butanes, particularly NDGA, have been shown to be effective sunscreening agents. In this regard, NDGA has been shown to strongly absorb sunlight at wavelengths known to produce sunburn. Thus, the catecholic butanes can be used to block sunlight and thereby prevent sunlight induction of cancer or promotion of existing cancers.

The methods according to the instant invention are also useful in conjunction with surgery for removal of internal cancers to eradicate residual tumor cells and to act as a prophylactic against local recurrence and metastatic spread of the tumor. The instant compositions may be applied to the effected area in lieu of surgery when there are cosmetic considerations due to the normally improved appearance of healed situs treated with the instant compositions compared to surgery alone.

The catecholic butanes useful in the methods of the instant invention, particularly NDGA, have also been found to be effective in treating hepatic and colon carcinoma. The catecholic butanes, when applied parenterally or by injection, are excreted primarily through the liver and gut, and therefore exert preferential cytotoxicity to tumors located in those organs.

The catecholic butanes useful in the methods of the instant invention are of the Formula (II), and are commonly available from Aldrich Chemical Co., Milwaukee, Wis. or can be synthesized by known methods. Illustrative classes of compounds within the scope of Formula (II) are those wherein:

(a) one or more of $R_1$, $R_2$, $R_3$, $R_4$, $R_5$, $R_6$, $R_7$, $R_8$, $R_9$, $R_{10}$, $R_{11}$, $R_{12}$ and $R_{13}$ are H, e.g., those wherein $R_5$ is H, $R_5$ and $R_6$ are H or $R_5$, $R_6$ and $R_7$ are H and $R_8$ and $R_9$ are OH or $OR_1$;

(b) $R_3$ and $R_4$ each are $CH_3$ or $C_2H_5$ including those wherein $R_5$, $R_6$ and $R_7$ are H and/or $R_8$ and $R_9$ are OH and $OR_1$;

(c) $R_1$ and $R_2$ are lower acyl, e.g., hydrocarbonacyl, preferably, alkanoyl, e.g., acetyl, propionyl, etc., including those of (a) and (b);

(d) $R_1$ and $R_2$ are alike and $R_8$ and $R_9$ are $OR_1$, including those of (a), (b) and (c); and (e) The compound is in the form of a single optical isomer or a mixture of such isomers, e.g., a racemic mixture, or diastereoisomers including each of (a), (b), (c) and (d).

As used herein, lower alkyl represents, inter alia, methyl, ethyl, n-propyl, isopropyl, n-butyl, iso-butyl, tertbutyl, n-pentyl, isopentyl, n-hexyl, and the like.

Lower acyl represents groups having the general formula RCO—, e.g., acetyl ($CH_3CO$—), propionyl ($CH_3CH_2CO$—), butyryl ($CH_3CH_2CH_2CO$—), and the like. When the catecholic butane compound is named as a substituted phenyl, the corresponding groups are acetoxy ($CH_3CO_2$—), propionyloxy ($CH_3CH_2CO_2$—), and butyroyloxy ($CH_3CH_2CH_2CO_2$—).

Examples of catecholic butanes include the d-, l-, racemic mixture of d- and l-, and meso-isomers of 1,4-bis(3,4-dihydroxyphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethyl-butane; 1,4-bis(3,4-dipropoxyphenyl)-2,3-dimethylbutane; 1-(3,4-dihydroxyphenyl)-4-(3',4',5'-trihydroxyphenyl) butane; 1,4-bis(3,4-diacetoxyphenyl)-2,3-dimethylbutane; 1,4-bis(3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; 1-(3,4-dihydroxyphenyl)-4-phenylbutane and 1-(3,4-dihydroxyphenyl-4-(2,5 dihydroxyphenyl) butane. Mixtures of the Formula (II) catecholic butanes may be used in the instant compositions.

The efficacious amount of catecholic butane used in the method of this invention may be varied over a wide range. The typical range of the amount of catecholic butane in the instant methods is between about 0.05 wt.% and 20 wt.% and preferably, the amount of catecholic butane applied according to the invention ranges between about 1 wt.% and 10 wt.%. As used herein, the weight percent in the formulations refers to the concentrations of materials being effectively delivered to the treatment site.

Generally, the efficacious amount and concentration of the catecholic butane to be applied are those which result in the composition exhibiting the property or properties required in the treatment for which the composition is being used, namely, anti-tumor activity. The preferred amounts depend upon the particular condition being treated, the method of delivery of the composition to the treatment site, e.g., topically or by injection, the rate of delivery of the active ingredients to the treatment site, and the number of applications of the formulation which can be used. Preferred amounts for any specific application may be determined by normal pharmacological screening methods used in the art. If desired, an excess of the catecholic butane can be used as appropriate for the specific condition being treated. It has been found that it is necessary to contact the tumor cells with at least a threshold amount of catecholic butane to observe an inhibition in growth of the neoplasm. This minimum amount has been found to be greater than about 10 nanomoles of catecholic butane per milliliter of tumor cells. Generally, preferred amounts of the catecholic butanes with respect to two classes of tumors and exemplary application amounts/rate are shown in Table I.

TABLE I

| Treatment/Use | Preferred Amount of Catecholic Butane | Exemplary Application Amount/Rate of Catechol Composition |
|---|---|---|
| Pre-Malignant Tumors | 0.05 to 15 wt. % of catecholic butane | Apply topically 100 mg/cm$^2$ to tumor. Repeat application when amount of prior application falls below about 1 mg/cm$^2$. Wound may be dressed until healing is complete. Healing period may extend for several months. Repeat daily as indicated by observation of tumor size reduction (i.e., if no reduction in size after 10 days, repeat 2-3 times daily; if reduction in size is observed, after 10 days, repeat at daily intervals or sooner if reduction in size ceases to continue). Healing period may extend for several months. Alternatively, 0.1 ml. of composition may be injected intralesionally at the tumor site. |
| Solid Epithelial Tumors | 0.1 to 20 wt. % of catecholic butane | |

The instant compositions can be applied topically to or injected into the treatment site, e.g., subcutaneously by injection. When used for topical applications, the catecholic butane is usually formulated with a pharmaceutically-acceptable carrier. The novel methods according to the invention have been found to be particularly effective when applied directly to the surface of the tumor or injected therein.

Carrier materials are well known in the pharmaceutical formulation art and include those materials referred to as diluents or vehicles. The carrier may include inorganic or organic materials and should have sufficient viscosity to allow spreading of the composition and provide good adherence to the tissue to which it is topically applied. Examples of such carriers include, without limitation, polyols such as glycerol, propylene glycol, polyethylene glycol, preferably of a molecular weight between about 400 and about 8000, suitable mixtures thereof, vegetable oils, and other materials well known to those skilled in this art. The viscosity of the formulation can be adjusted by methods well known in the art, for example, by the use of a higher molecular weight polyethylene glycol.

In addition to the catecholic butane and carrier, the formulation can contain pharmacologically-acceptable additives or adjuvants such as antimicrobial agents, e.g. methyl, ethyl, propyl, and butyl esters of para-hydroxybenzoic acid as well as chlorobutanol, phenol, ascorbic acid, etc. The formulation can also contain thickening or gelling agents, emulsifiers, wetting agents, coloring agents, buffers, stabilizers and preservatives including antioxidants such as butylhydroxyanisole in accordance with the practice of the art. The formulation can also contain penetration enhancers such as dimethyl sulfoxide, long-chain alcohols such as nonoxynol, long-chain carboxylic acids, propylene glycol, N-(2-hydroxyethyl)pyrrolidone,1-dodecyl-azacycloheptan-2-one, and the like. Depending on the method of application and the disease being treated, it may be desirable to use absorption-delaying agents such as aluminum monostearate and gelatin.

The composition of the formulation can be adjusted using components well-known in the formulation art to provide a pharmaceutical formulation which is a gel, cream, ointment, solid, liquid, semi-solid, etc. The particular physical form of the formulation depends on the desired method of treatment and the patient to be treated.

Typical formulations of the pharmaceutical compositions of this invention are set forth in Table II.

TABLE II

| Application Form | Formulation | Grams |
|---|---|---|
| Ointment | Catecholic butane | (preferred amount: about 1-5 gr.) |
| | Peg 400 | 4.2 |
| | Peg 8000 | 61.7 |
| | Water | 19.0 |
| | Ascorbic acid | 0.1 |
| Gel | Catecholic butane | (preferred amount: about 0.1-2 gr.) |
| | Standard denatured alcohol | 12.0 |
| | Propylene glycol | 22.5 |
| | Water | 53.4 |
| | Non-ionic surfactant | 6.0 |
| | Xantham gum | 4.0 |
| | Ascorbic acid | 0.1 |
| Cream | Catecholic butane | (preferred amount: about 1-5 gr.) |
| | Ascorbic acid | 0.1 |
| | Benzyl alcohol | 5.0 |
| | Propylene glycol | 23.0 |
| | Water | 35.4 |
| | Stearyl alcohol | 7.0 |
| | Cetyl alcohol | 4.5 |
| | White petrolatum | 13.0 |
| | Poloxyl-40 stearate | 7.0 |
| Solid | Catecholic butane | (preferred amount: 1-10 gr.) |
| | Carnuba wax | 8.9 |
| | Beeswax | 13.3 |
| | Lanolin anhydrous | 4.4 |
| | Cetyl alcohol | 4.4 |
| | Ascorbic acid | 0.1 |
| | Castor oil | 57.7 |
| | Water | 1.2 |
| Injectible Liquid | Catecholic butane | (preferred range: 0.1-5 gr.) |
| | Water | 31.9 |
| | Glycerine | 36.5 |
| | Glycine | 1.5 |
| | Sodium ascorbate | 0.1 |
| | Propylene glycol | 25.0 |

For administration by injection, the compositions according to the invention are formulated as solutions or suspensions having a low enough viscosity to be injected. The composition suitable for injectable use must be sterile and fluid to the extent that easy syringe injection exists. It should also be stable under conditions of manufacture and storage and be preserved against contamination by microorganisms. Preservatives include alcohol, benzoic acid, sorbic acid, and methyl and propyl paraben with and without propylene glycol. Additionally, the pH of the composition must be within a range which does not result in tissue damage, namely, between about 3-7.5.

The concentrations of active ingredients in a particular formulation required to provide a particular effective dose may be determined by a person skilled in the pharmaceutical formulation art based upon the properties of a carrier and the particular additives introduced into the formulation. It is contemplated that formulations can be prepared that have significantly higher concentrations of catecholic butane depending upon the carrier and additives being used. If the carrier substantially retains the catecholic butane or releases it at a slow rate, the concentrations of the catecholic butane in the formulation can be substantially increased and in fact may have to be substantially increased in order to provide an effective treatment. In practice, it is preferred that a formulation contain the lowest concentrations of catecholic butane which effectively treat the condition with the desired number of applications, i.e., a lower effective dose rate can be tolerated if multiple applications are used. This low concentration limit is dependent upon the delivery effectiveness of the carrier vehicle. Preferably, the catecholic butane comprises between about 1 and about 10 weight percent of the formulation.

A preferred embodiment of the instant invention comprises compositions containing NDGA, i.e., meso 1,4-bis(3,4-dihydroxyphenyl)-2,3-dimethylbutane. This composition has been found to be particularly effective in treating solid tumors and actinic keratosis. Although the effective concentration of nordihydroguaiaretic acid delivered to the treatment site depends, inter alia, upon the carrier and other additives included in the formulation, ordinarily the concentration of NDGA in the formulation will range from about 1 to about 15 weight percent. These ranges are provided by way of description and not by way of limitation since it is recognized that the concentration may be adjusted over a wide range depending on the carrier material, number of applications used, etc., as described hereinabove.

The pH of the formulation is important in assuring stability of the catecholic butane as well as assuring that the formulation is physiologically acceptable to the patient. Many of the catechols, particularly nordihydroguaiaretic acid, are susceptible to oxidation, for example, by air. Such oxidation can result in discoloration of the formulation rendering it unacceptable for pharmaceutical use. These catechols are more stable against oxidation at lower pH levels. Therefore, it is preferred that if the formulation is to be exposed to oxidizing conditions the pH be maintained below about 7.5 and preferably below about 6 in order to provide maximum stability for the catechol against oxidation. However, if oxidizing conditions can be avoided, for example, by storage of the formulation under an inert atmosphere such as nitrogen, a higher pH can be used. The pH of the formulation may be maintained through the use of toxicologically-acceptable buffers. Such buffers are well known in the pharmaceutical formulation art, and include hydrochloric acid buffer, acid phthalate buffer, phosphate buffer and citric acid/sodium citrate buffer.

Alternately, antioxidants such as ascorbic acid, hydroxyquinone, sodium bisulfite, meta bisulfite, etc. can be added to the formulation.

In topical applications the instant compositions are applied to the affected area or afflicted situs of the patient. The term "topical" refers herein to the surface of the epidermal tissue, especially the skin, the surface of tumors on the skin which have been debrided or otherwise modified, as well as sites from which solid tumors have been removed either from the skin or internally.

In preparing a formulation suitable for topical application, the catecholic butane is normally mixed with a suitable solvent. Examples of solvents which are effective for this purpose include ethanol, acetone, acetic acid, aqueous alkaline solutions, dimethyl sulfoxide, glycerine, glycerol, propylene glycol, nonoxynol, ethyl ether, polyethylene glycol, etc.

Application by injection can be used for treatment of solid tumors in which removal by surgery is not desired or for which surgery is not medically advisable. In this procedure the instant composition is injected directly into the tumorous cells.

The methods of the instant invention have also been found to be useful in the treatment of lesions and draining wounds which show impaired healing. As used herein the term "lesion" refers to any pathological or traumatic discontinuity of tissue. A "wound" is a lesion which results from a bodily injury caused by physical means. Lesions which do not readily heal can be manifestations of conditions, diseases or infections, for example, cutaneous ulcers, osteomyletis, acne vulgaris, draining fistulas, etc. Not uncommonly, lesions do not heal properly and continue to drain which results in discomfort to the patient and a continued threat of severe infection. Such conditions in which tissue does not readily grow to heal the lesion or wound can be the result of bacterial infection or other causes not fully understood. Exposed areas created by the sloughing off of necrotic matter, generally result in pus formation (suppuration).

Direct contact of the exposed area of the wound or lesion with the instant compositions has been found in clinical studies to substantially aid the healing process, possibly by inducing the formation of granulation tissue. This promotion of healing has significant advantages, for example, in the treatment of solid tumors directly or the situs from which such tumors have been surgically removed in that healing is promoted concurrently with inhibiting the growth of any tumor cells which might remain at the site of surgery.

In determining the efficacy of a catecholic butane formulation in the treatment of a tumor, initial screening is commonly done by the Human Tumor Clonogenic Assay (HTCA). It has been reported that clinical correlations form retrospective analysis and prospective clinical trials with such clonogenic assays have indicated that there is a 60 to 70% correlation between in vitro sensitivity and clinical response. The studies have also indicated that there is a greater than 90% correspondence between in vitro resistance and treatment failure. However, the screening of new antitumor agents is still primarily being conducted using a variety of tumor models in vivo. The National Cancer Institute is currently using in vivo tumor models which include the L-1210 lymphocytic leukemia, B-16, melanoma, S-180 Carcinoma, 3 transplantable murine tumors, and the MX-1 human mammary tumor xenograph.

The following examples are included by way of illustration and not by way of limitation. Unless otherwise indicated, the nordihydroguaiaretic acid used in the instant Examples was the meso-isomer and is designated NDGA. Other isomers are indicated, e.g., d,l-NDGA.

EXAMPLE I

The catecholic butane 1-(3,4-dihydroxyphenyl)-4-(2,3,4-trihydroxyphenyl) butane was prepared by the following procedure.

500 grams of 3,4-dimethoxydihydrocinnamic acid was suspended in 1.6 liters of methanol containing 250 ml of 2,2-dimethoxypropane. To this mixture was added dropwise a solution made by adding 20 ml. of acetyl chloride to 400 ml of methanol. The resulting mixture was stirred overnight at room temperature and finally at reflux for one hour. The solvent was evaporated to give a syrup in quantitative yield, 533 g.

To 912 ml. of lithium aluminum hydride (1M in THF) was added dropwise 213 g. of 3,4-dimethoxydihydrocinnamic acid methyl ester dissolved in 900 ml of dry THF at such a rate as to maintain gentle reflux (5 hours). The reaction mixture was stirred overnight at room temperature, cooled in an ice bath and treated dropwise with ammonium chloride solution (saturated) (104 ml) over a two hour period. After stirring for several hours, the reaction mixture was diluted with 500 ml. of THF, filtered and the filtrate evaporated in a vacuum to give 160 g. (86%) of a light yellow oil.

3-(3,4-dimethoxyphenyl)propanol (202 g) was added to 218 ml of triethylamine in one and half liters of methylene chloride. This solution was cooled to −10° C. in an ice salt bath and 87.6 ml. of methanesulfonyl chloride was added dropwise over a one and a half hour period while stirring rapidly. Stirring was continued for another hour and the mixture was washed with 700 ml. of ice water, 700 ml. of 3N hydrochloric acid, 700 ml. of saturated sodium bicarbonate and finally with 700 ml. of brine. The organic phase was dried with sodium sulfate and evaporated in a vacuum to give an orange oil in quantitative yield, 282 g.

3-(3,4-dimethoxyphenyl)propanol methanesulfonate, 282 g., (1.029 mol.); KBr, 282 g. (2.37 mol.) and dicyclohexano-18-crown-6, 19.2 g. (0.01515 mol.) were stirred in refluxing acetonitrile, 2.8 liters (dried over 3A molecular sieves) for 22 hours. The mixture was filtered and the filtrate evaporated in a vacuum to give an orange oil, 267 g. The product could be purified by vacuum distillation at 0.5 mm Hg, b.p.=113-116° C.

3-(3,4-Dimethoxyphenyl)propyl bromide, 25.9 g., in 50 ml. of dry tetrahydrofuran (dried by distillation from LAH) was placed in a dropping funnel. Magnesium powder, 2.5 g., and a trace of iodine was placed in a dry three neck flask with nitrogen inlet and reflux condenser. The reaction started upon addition of the liquid reactant and reflux was continued over a three hour period during which time the metal dissolved in the stirred solution. The reaction was cooled and the volume made up to 200 ml. to form a 0.5M solution in dry THF.

2,3,4-Trimethoxybenzaldehyde, 1.96 g. (0.01 mole), dissolved in 20 ml. of dry THF and 20 ml. of the 0.5M Grignard reagent from 3-(3,4-dimethoxyphenyl)propyl bromide in THF was added dropwise at ice temperature. The mixture sat over night at room temperature. The solution was evaporated in a vacuum and 20 ml. of ethanol was added carefully followed by excess sodium borohydride. Refluxing for a few minutes destroyed the yellow color of the small amounts of ketone and other unsaturated impurities formed from oxidation of the product. Most of the ethanol was evaporated and the residue partitioned between water and ether, 50 ml. of each. The ether phase was dried over sodium sulfate and evaporated to give 4.65 g. of a pale yellow oil.

The 4-(3,4-dimethoxyphenyl)-1-(2,3,4-trimethoxyphenyl)butanol, 3.65 g., was treated with excess sodium hydride, 1 g., and methyl iodide, one ml, in 25 ml. of dry dimethylformamide during one hour of stirring. Water was added carefully dropwise at first and finally 500 ml. of water was added. The product was extracted three times with 50 ml. of chloroform and the solvent evaporated to give a colorless crude oily product that can be used in the next step without further purification.

About 100 ml of anhydrous ammonia was condensed into a three necked flask with a dry ice condenser and dry ice bath. The flask was protected from moisture with a soda-lime tube and flow of dry nitrogen. One gram of clean sodium metal was dissolved in the liquid ammonia and the whole of the crude product in 20 ml of dry tetrahydrofuran was added as quickly as possible. The dark blue solution was stirred rapidly for twelve minutes before enough methanol was added to destroy the blue color. Evaporation of the solvent under a vacuum gave a thick residue to which 500 ml. of water was added. The water solution was extracted twice with 50 ml. of chloroform that left three grams of oily residue on evaporation. Chromatography of this crude product on 300 g. of silica-gel using chloroform as an eluate gave 2.3 of pure 1-(3,4-dimethoxyphenyl)-4-(2,3,4-trimethoxyphenyl) butane (one spot on TLC).

A 1.15 g. sample of 1-(3,4-dimethoxyphenyl)-4-(2,3,4-trimethoxyphenyl) butane was refluxed for nine hours in 50 ml. of 48% hydrobromic acid under an inert nitrogen atmosphere. Standing over the weekend allowed 641 mg. of tan product to settle out in the freezer. This material was recrystallized under inert atmosphere from methanol-water 1:20 to give light pink crystals, m.p.=165-167° C.

The following compounds were prepared by a similar procedure:

(a) 1-(3,4-Dihydroxyphenyl)-4-(3,4,5-trihydroxyphenyl)butane;
(b) 1-(3,4-Dihydroxyphenyl)-4-phenylbutane
(c) 1-(3,4-Dihydroxyphenyl-4-(2,5-dihydroxyphenyl) butane;
(d) 1,4-Di(3,4-dihydroxphenyl)-1,2,3,4-tetramethylbutane
(e) 1,4-Di(3,4-dihydroxyphenyl)-2-methyl-3-ethylbutane
(f) 1,4-Di(3,4-dihydroxyphenyl)-1-propyl-2-methyl-3-ethylbutane.

EXAMPLE 2

NDGA was evaluated for its effect on human mammary carcinoma MX-1 xenograft in athymic nude NCr mice.

A 14 mg. fragment of the human mammary carcinoma MX-1 was planted subcutaneously into the axillary region of mice with a puncture in the inguinal region at day 0. Mice with tumors weighing no less than 75 mg. and no more than 350 mg. were selected and pooled on day 1.

Tumored groups of mice were injected with a 0.1 ml. volume of the appropriate test or vehicle control substance on day 1 only. Individual body weights were recorded on day 1 and two times per week thereafter until day 60, and individual tumors were measured with calipers on day 1, and twice per week thereafter through day 60. Mean tumor weights were calculated for each measurement day. Each day, change in mean tumor weight was determined for both the test and control.

0.1 ml. of Compositions A through I were injected intratumorally on day 1 with NDGA as set forth in the table below:

| Composition | No. Mice | % NDGA in Composition |
|---|---|---|
| A | 6 | 1.53 ± 0.06 |
| B | 6 | 2.49 ± 0.08 |
| C | 6 | 3.41 ± 0.18 |
| D | 6 | 4.61 ± 0.34 |
| E | 6 | 6.36 ± 0.69 |
| F | 6 | 7.62 ± 0.17 |
| G | 6 | 9.44 ± 0.16 |

-continued

| Composition | No. Mice | % NDGA in Composition |
|---|---|---|
| H | 6 | 15.40 ± 0.40 |
| I | 6 | 18.40 ± 0.30 |

The relative size (T/C%) of the tumor in the treated versus untreated animals was calculated as follows:

$$\frac{T}{C}\% = \frac{\text{wt. of tumor in treated animal}}{\text{wt. of tumor in untreated animal}} \times 100\%$$

Efficacy is indicated by T/C of less than 100%; the smaller the value, the more effective the composition as an antitumor agent.

The activity and duration of action of composition I is shown below:

| Day | Animals Died | Relative Tumor Size, T/C % |
|---|---|---|
| 1 | 0 | 0.0 |
| 4 | 0 | 109.9 |
| 8 | 0 | 59.9 |
| 11 | 0 | 16.1 |
| 15 | 0 | 14.2 |
| 18 | 0 | 15.5 |
| 22 | 0 | 13.0 |
| 25 | 0 | 17.1 |

The results for each of the compositions on day 26 are set forth in table 2:

TABLE 2

Dose-response evaluation of Antitumor activity of NDGA on Day 26

| Composition | NDGA Dose % | Tumor Wt. (grams) | Relative Tumor Size, T/C % |
|---|---|---|---|
| A | 1.53 | 5121.0 | 112.0 |
| B | 2.49 | 5827.0 | 129.8 |
| C | 3.41 | 5071.5 | 110.3 |
| D | 4.61 | 3390.9 | 71.7 |
| E | 6.36 | 3249.4 | 70.5 |
| F | 7.62 | 2650.3 | 56.0 |
| G | 9.44 | 1650.1 | 32.7 |
| H | 15.40 | 955.5 | 16.8 |
| I | 18.40 | 942.0 | 17.1 |

EXAMPLE 3

The antiproliferative effect of NDGA on CMT-12 cultured canine breast adenocarcinoma tumor cells was evaluated in clonogenic (cancer cell) assays.

Single cell suspensions of tumor cells harvested from culture flasks were exposed to the different compositions of NDGA for one hour at 37° C in liquid medium, and the cells were then washed twice, suspended in agarose medium and plated and the number of colony forming cells were determined. Results are expressed as percent inhibition of survival of clonogenic cells in treated cultures relative to nontreated control cultures. Significant anticancer activity was defined as >70% inhibition of the survival of colony-forming (tumor) cells.

The results of the clonogenic assay using CMT 12 canine mammary carcinoma cells are presented in Table 3.

TABLE 3

| Composition | No. Tumor Colonies Surviving | % Inhibition |
|---|---|---|
| 5 MicroMolar NDGA | 229.7 ± 10.9 | 0 |
| 10 MicroMolar NDGA | 173.3 ± 23.3 | 82.5 |
| 18 microMolar NDGA | 190 ± 16.3 | 90.9 |
| 27 microMolar NDGA | 40 ± 16.3 | 98.1 |
| 56 microMolar NDGA | 3.3 ± 4.7 | 99.8 |

EXAMPLE 4

Compositions of NDGA were tested for their ability to inhibit in vitro growth of the MC-1 equine sarcoid-derived cell line, in experiments similar to those of Example 3.

Compositions containing NDGA were uniformly successful in inhibiting colony growth over the duration of the assay, an effect which was especially noticable at concentrations of 27 and 56 microMolar NDGA.

TABLE 4

| | Percentage Inhibition of Colony Growth At Day 14 | | | |
|---|---|---|---|---|
| Amount NDGA (MicroMolar) | Experiment and % Inhibition | | | % Inhibition (Mean) |
| | #1 | #2 | #3 | |
| 18 | 20.9 | 36.7 | 39.5 | 32.4 |
| 27 | 32.8 | 58.9 | 49.3 | 47.0 |
| 56 | 33 | 62.2 | 40.7 | 45.3 |

EXAMPLE 5

The antitumor effect of NDGA against the human lung tumor cell line LX-T was determined utilizing a clonogenic assay.

The human lung tumor cell line, LX-T, which was derived from the solid tumor, LX-1, was cultured in the standard medium RPMI-1640 +10% fetal calf serum (FCS). A stock solution ($10^{-2}$M) of NDGA was prepared by dissolving 32.04 mg of NDGA in 4 ml DMSO and 6 ml distilled $H_2O$. Serial dilutions of the test stock solutions were made in 15 ml of $Ca^{2+}$—and $Mg^{2+}$—free Hank's balanced salt solution (HBSS).

The LX-T cells were incubated in the presence of various amounts of NDGA, and the antitumor effect was determined by measuring the DNA control of the LX-T nuclei using DNA flow cytometric analysis with a DNA-specific fluorochrome, 4', 6-diamidino-2-phenylindole (DAPI).

Table 5A shows the effective doses at different responses ($ED_x$) where x represents 50, 75, 90 or 95% cell growth inhibition.

TABLE 5A

| Calculated $ED_x$ for NDGA (MicroMolar ± SD) | |
|---|---|
| ED(50) | 17.6 ± 4.07 |
| ED(75) | 26.6 ± 12.11 |
| ED(90) | 41.1 ± 28.10 |
| ED(95) | 55.9 ± 46.79 |

For comparison, Table 5B lists the ED (50) for three known anticancer drugs along with the ED(50) for NDGA.

TABLE 5B

| Drug Name | ED(50) microMolar |
|---|---|
| 5-FU | 102.23 |

TABLE 5B-continued

| Drug Name | ED(50) microMolar |
|---|---|
| Adriamycin | 25.6 |
| Mutamycin | 18.43 |
| NDGA | 17.6 |

EXAMPLE 6

The in vivo antitumor effect of NDGA at various survival levels was determined using MX-1 (human breast adenocarcinoma) cells implanted subcutaneously in the flank of nude mice.

Tumors which reached the 25-100 mm$^2$ range were used for the experiment. 0.1 ml of the test compound in solution was injected directly into the tumor. The tumors were measured periodically to determine their weight until 60 days after the initial treatment or all mice had died. Mice which showed no evidence of tumors were kept for 60 days to evaluate potential for tumor recurrence, at which time tumor characteristics, if any, were recorded.

The effective doses ($ED_x$) of NDGA at different response levels are provided in Table 6.

TABLE 6

| $ED_x$ (micromoles) for NDGA | |
|---|---|
| Response Level | Micromoles |
| ED(50) | 13.62 |
| ED(75) | 25.66 |
| ED(90) | 48.33 |
| ED(95) | 74.34 |

EXAMPLE 7

A composition containing 17.6% NDGA and 1% BHT in Pego 400 was tested for antineoplastic activity in athymic mice implanted with human breast adenocarcinoma, MX-1. Each animal was innoculated intradermally on the dorsum near the nape of the neck with 0.5 ml of a MX-1 homogenate. The animals were treated by topical application with the NDGA composition after day 23. The results are given in Table 7.

TABLE 7

| Test Composition | Tumor Free 60 Days | Tumor Recurrence |
|---|---|---|
| 17.6% NDGA/1% BHT in PEGO 400 | 3/5 | 0 |

EXAMPLE 8

Compositions containing 4.4 wt/wt% of meso and DL NDGA were tested for efficacy against the MX-1 tumor as in Example 7.

The results are set forth in Table 8.

TABLE 8

| Organic Compound | Tumor Free 60 Days | Tumor Recurrence |
|---|---|---|
| NDGA | 4/5 | 0 |
| dl-NDGA | 4/5 | 0 |

EXAMPLE 9

Mice were exposed to dimethyl benzanthracene (DMBA), a classical tumor inducer, and to phorbol ester (TPA), a classical tumor promoter, after having been treated with NDGA.

Twenty mice were included in each of the following groups:
1. Positive control group: DMBA+TPA. Female SENCAR mice 6-8 weeks old received a single topical application of 10 mg of DMBA in 0.2 ml of acetone as the initiating agent. After one week, animals received twice weekly applications of tumor promoter TPA in 0.1 ml of acetone. Tumor formation was recorded weekly.
2. Antipromoting activity: DMBA+NDGA+TPA. 30 minutes prior to each application of TPA animals received topical application of NDGA (9 mg.) in 0.2 ml of acetone.
3. Anticarcinogenic activity: NDGA+D-MBA+TPA. For five consecutive days animals received topical applications of NDGA (3 mg.) in 0.2 ml of acetone. 24 hours after the last treatment with NDGA, animals received DMBA and TPA exactly as in the positive control group.

NDGA was shown to nearly completely prevent TPA tumor promotion and to significantly reduce the potential of tumor induction by DMBA.

EXAMPLE 10

The ability of NDGA to absorb harmful sunlight radiation was tested.

A solution of NDGA in methanol was demonstrated to absorb strongly at 2816 Angstroms in the ultraviolet region, a sunlight wavelength known to result in sunburn.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A method for inhibiting the growth of a tumor which comprises topically administering to the situs of the tumor of a mammal in need of said treatment an effective amount of a composition comprising at least 1 catecholic butane of the formula:

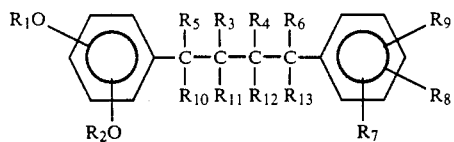

wherein $R_1$ and $R_2$ are independently H, lower alkyl, lower acyl, or alkylene;

$R_3$, and $R_4$, $R_5$, $R_6$, $R_{10}$, $R_{11}$, $R_{12}$ and $R_{13}$ are independently H or lower alkyl;

$R_7$, $R_8$ and $R_9$ are independently H, hydroxy, lower alkoxy, lower acyloxy, or any two adjacent groups together may be alkylene dioxy.

2. The method according to claim 1 wherein the composition contains 0.1-10 wt. % of said catecholic butane.

3. The method according to claim 1 wherein the catecholic butane is nordihydroguaiaretic acid.

4. The method according to claim 1 wherein said catecholic butane contains at least one lower alkyl ether derivative moiety.

5. The method according to claim 1 wherein said catecholic butane contains at least one lower acyl ester derivative moiety.

6. The method according to claim 1, wherein lower alkyl is $C_1$-$C_6$ alkyl, $R_3$ and $R_4$ are $C_1$-$C_3$ alkyl and the lower acyl is a $C_1$-$C_6$ acyl.

7. The method according to claim 1, wherein the catecholic butane is selected from the group consisting of 1,4-bis(3,4-dihydroxphenyl)-2,3-dimethylbutane; 1,4-bis(3,4-dihydroxyphenyl)butane; 1,4-bis(3,4-dimethoxyphenyl)-2,3 -dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3,4,5-trihydroxyphenyl) butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4-divaleroyloxphenyl)-2,3-dimethylbutane; 1,4-bis(3,4-dipivaloyloxphenyl)-2,3-dimethylbutane; 1,4-bis (3,4-dipivaloyloxyphenyl) butane; 1,4-bis(3,4-dineopentylcarboxylphenyl)-2,3-dimethylbutane; and 1-(3,4-dihydroxylphenyl)-4-phenylbutane; 1-(3,4-dihydroxyphenyl)-4-(2,5 dihydroxyphenyl) butane.

8. The method according to claim 1 wherein the composition includes a pharmaceutically acceptable carrier.

9. The method according to claim 1 wherein said administering is effectuated by means selected from the group consisting of administration to the surface of the skin at the situs of the tumor and injection of the composition into the interior or near vicinity of the tumor.

10. The method according to claim 1 wherein the tumor are selected from the group consisting of equine sarcoid, equine papilloma, equine malignant melanoma, equine squamous cell carcinoma, canine perianal adenoma, canine mast cell carcinoma, canine breast adenocarcinoma and canine malignant melanoma.

11. The method according to claim 10, wherein the catecholic butane is nordihydroguaiaretic acid.

12. The method according to claim 11, wherein 10 nanomoles of composition are applied to each milliliter of solid tumor.

13. The method according to claim 10 wherein said administering is effectuated by means selected from the group consisting of topical administration to the surface of the skin at the situs of the tumor and injection of the composition into the interior or near vicinity of the tumor.

14. The method according to claim 10 wherein said catecholic butane is substantially nordihydroguaiaretic acid.

15. The method according to claim 1 wherein the tumor is selected from the group consisting of malignant melanoma, mammary tumor, basal cell carcinoma, squamous cell carcinoma, and epidermal tumors of the skin.

16. A method for treating tumors of the skin, which comprises administering to the skin of a mammal in need of said treatment an effective amount of a composition comprising at least one catecholic butane of the formula:

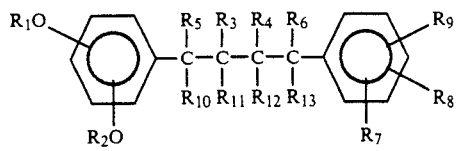

wherein $R_1$ and $R_2$ are independently H, lower alkyl, lower acyl or alkylene;

$R_3$, $R_4$, $R_5$, $R_6$, $R_{10}$, $R_{11}$, $R_{12}$ and $R_{13}$ are independently H or lower alkyl;

$R_7$, $R_8$ and $R_9$ are independently H, hydroxy, lower alkoxy, lower acyloxy, or any two adjacent groups may be alkylene dioxy.

17. The method according to claim 16 wherein the composition includes a pharmaceutically acceptable carrier.

18. The method for treating a keratosis of the skin which comprises administering to the skin of a mammal in need of said treatment at the situs of the keratosis an effective amount of a composition comprising at least one catecholic butane of the formula:

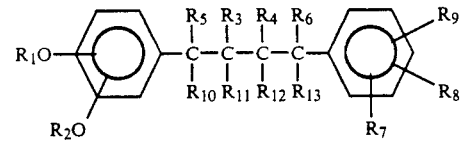

wherein $R_1$ and $R_2$ are independently H, lower alkyl or lower acyl;

$R_3$, $R_4$, $R_5$, $R_6$, $R_{10}$, $R_{11}$, $R_{12}$ and $R_{13}$ are independently H or lower alkyl; and $R_7$, $R_8$ and $R_9$ are independently H, hydroxy, lower alkoxy or lower acyloxy.

19. The method according to claim 18 wherein the catecholic butane is selected from the group consisting of nordihydroguaiaretic acid in any of its racemic forms, nordihydroguaiaretic acid tetrapivalate, nordihydroguaiaretic acid tetrapropionate and all optical configurations thereof.

20. The method according to claim 19 wherein the catecholic butane is nordihydroguaiaretic acid.

21. The method according to claim 18 wherein the composition contains 0.1-10 wt. % of said catecholic butane.

22. The method according to claim 18 wherein said catecholic butane contains at least one lower alkyl ether derivative moiety.

23. The method according to claim 18 wherein said catecholic butane contains at least one lower acyl ester derivative moiety.

24. The method according to claim 18, wherein lower alkyl is $C_1$-$C_6$ alkyl, $R_3$ and $R_4$ are $C_1$-$C_3$ alkyl and the lower acyl is a $C_1$-$C_6$ acyl.

25. The method according to claim 18, wherein the catecholic butane is selected from the group consisting of 1,4-bis(3,4-dihydroxyphenyl)-2,3-dimethylbutane; 1,4-bis(3,4-dihydroxyphenyl)butane; 1,4-bis(3,4-dimethoxyphenyl)-2,3 -dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3,4,5-trihydroxyphenyl) butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4- divaleroyloxyphenyl)-2,3-dimethylbutane; 1,4-bis(3,4-dipivaloyloxphenyl)-2,3-dimethylbutane; 1,4-bis (3,4-dipivaloyloxyphenyl) butane; 1,4-bis(3,4-dineopentyl-carboxylphenyl)-2,3-dimethylbutane; and 1-(3,4-dihydroxyphenyl)-4-phenylbutane; 1-(3,4-dihydroxyphenyl)-4-(2,5 dihydroxyphenyl) butane.

26. The method according to claim 18 wherein the composition includes a pharmaceutically acceptable carrier.

27. The method according to claim 18 wherein the keratosis is actinic keratosis.

28. A method for treating actinic keratosis which comprises administering to the skin of a mammal in need of said treatment at the situs of the actinic keratosis an effective amount of a composition comprising at least one catecholic butane of the formula:

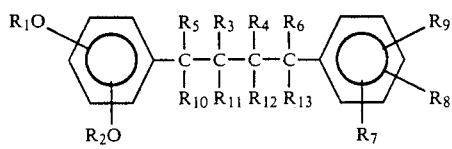

wherein $R_1$ and $R_2$ are independently H, lower alkyl, or lower acyl and $R_1$ and $R_2$ together may be alkylene;

$R_3, R_4, R_5, R_6, R_{10}, R_{11}, R_{12}$ and $R_{13}$ are independently H or lower alkyl; and $R_7, R_8$ and $R_9$ are independently H, hydroxy, lower alkoxy, lower acyloxy, or any two adjacent groups may be aklylene dioxy.

29. The method according got claim 28 wherein the catecholic butane is selected from the group consisting of nordihydroguaiaretic acid in any of its racemic forms, nordihydroguaiaretic acid tetrapivalate, nordihydroguaiaretic acid tetrapropionate and all optical configurations thereof.

30. A method for treating actinic keratosis which comprises administering to the skin of a mammal in need of said treatment at the situs of the actinic keratosis an effective amount of a composition comprising nordihydroguaiaretic acid.

31. A method for treating tumors of the skin which comprises administering to the. skin of a mammal in need of said treatment an effective amount of a composition comprising at least one catecholic butane of the formula:

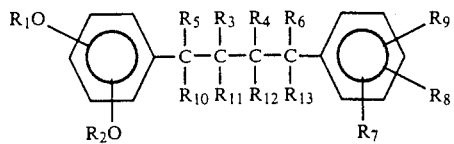

wherein $R_1$ is H, lower alkyl or lower acyl, $R_2$ is lower acyl and $R_1$ and $R_2$ together may be alkylene;

$R_3, R_4, R_5, R_6, R_{10}, R_{11}, R_{12} R_{13}$ are independently H or lower alkyl; and $R_7, R_8$ and $R_9$ are independently H, hydroxy, lower alkoxy or lower acyloxy; or any two adjacent groups together may be alkylene dioxy.

32. A method for treating tumors of the skin which comprises administering to the skin of a mammal in need of said treatment an effective amount of a composition comprising at least one catecholic butane of the formula:

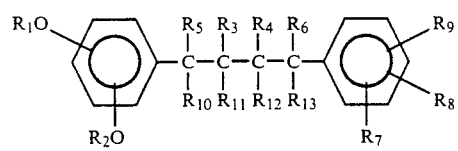

wherein $R_1$ and $R_2$ are independently H, lower alkyl or lower acyl and $R_1$ and $R_2$ together may be alkylene;

$R_3, R_4, R_5, R_6, R_{10}, R_{11}, R_{12}$ and $R_{13}$ are H; and $R_7, R_8$ and $R_9$ are independently H, hydroxy, lower alkoxy or lower acyloxy; or any two adjacent groups together may be alkylene dioxy.

33. A method for treating tumors of the skin which comprises administering to the skin of a mammal in need of said treatment an effective amount of a composition comprising at least one catecholic butane of the formula:

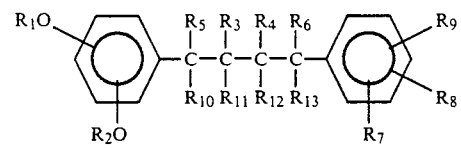

wherein $R_1, R_2, R_7$ and $R_8$ are lower acyl;

$R_3$ and $R_4$ are methyl; and $R_5, R_6, R_9, R_{10}, R_{11}, R_{12}$ and $R_{13}$ are H.

34. The method for treating tumors of the skin according to claim 33 wherein the tumor is actinic keratosis.

* * * * *